United States Patent [19]

Breyer et al.

[11] Patent Number: 5,785,657
[45] Date of Patent: Jul. 28, 1998

[54] BLOOD FLOW MEASUREMENT DEVICE

[75] Inventors: Branko Breyer; Bozidar Ferek-Petric, both of Zagres, Croatia

[73] Assignee: Pacesetter AB, Solna, Sweden

[21] Appl. No.: 669,473

[22] PCT Filed: Jan. 13, 1995

[86] PCT No.: PCT/EP95/00134

§ 371 Date: Nov. 4, 1996

§ 102(e) Date: Nov. 4, 1996

[87] PCT Pub. No.: WO95/19138

PCT Pub. Date: Jul. 20, 1995

[30] Foreign Application Priority Data

Jan. 14, 1994 [HR] Croatia .................. P940025A

[51] Int. Cl.$^6$ ...................................... A61B 8/06
[52] U.S. Cl. ............................ 600/454; 600/468
[58] Field of Search .............. 128/661.07–661.1, 128/660.01, 662.06; 73/861.257, 861.28; 600/454–458, 466, 468

[56] References Cited

U.S. PATENT DOCUMENTS

| | | |
|---|---|---|
| 4,227,407 | 10/1980 | Drost . |
| 4,265,126 | 5/1981 | Papdofrangokis et al. .... 128/661.09 X |
| 4,573,477 | 3/1986 | Namekawa et al. . |
| 4,744,367 | 5/1988 | Kodama et al. ................ 128/661.09 |
| 4,790,323 | 12/1988 | Leavitt et al. . |
| 5,127,418 | 7/1992 | Sakai et al. ................... 128/661.09 |
| 5,291,892 | 3/1994 | O'Donnell .................... 128/661.09 |
| 5,390,677 | 2/1995 | Ferrara et al. ................ 128/661.09 |

FOREIGN PATENT DOCUMENTS

| | | |
|---|---|---|
| 0 092 841 | 4/1983 | European Pat. Off. . |
| 0 140 726 | 8/1984 | European Pat. Off. . |
| 0 144 968 | 12/1984 | European Pat. Off. . |
| 0 150 672 | 12/1984 | European Pat. Off. . |
| 0 228 070 | 12/1986 | European Pat. Off. . |
| 0 266 998 | 11/1987 | European Pat. Off. . |
| 0 447 597 | 3/1990 | European Pat. Off. . |
| 2 551 213 | 4/1983 | France . |
| OS 35 44 477 | 6/1986 | Germany . |
| 57-70479 | 4/1982 | Japan . |
| 2-16139 | 4/1990 | Japan . |
| 2 170 972 | 8/1986 | United Kingdom . |
| WO 92/15239 | 9/1992 | WIPO . |

OTHER PUBLICATIONS

"Theory Of Ultrasound Doppler–Spectra Velocimetry For Arbitrary Beam And Flow Configurations," Censor et al. IEEE Trans. On Biomed. Eng., vol. 15, No. 9, Sep. 1988, pp. 740–751.

"Real–Time Two–Dimensional Blood Flow Imaging Using An Autocorrelation Technique," Kasai et al, 1985 Ultrasonics Symposium, pp. 953–958.

"Pulsed Ultrasonic Transit Time Flowmeter," Franklin et al. IRE Trans. On Biomedical Electronics, Jan. 1962, pp. 44–49.

(List continued on next page.)

*Primary Examiner*—Francis Jaworski
*Attorney, Agent, or Firm*—Hill & Simpson

[57] ABSTRACT

A blood flow velocity measurement device is devised where there exist such entities within the fluid which are detectable when axially flowing (passing by) an appropriate detector of known and well defined dimensions mounted onto a catheter. The entities produced for instance by a generator, when flowing by the detector, induced a known single response, the response bearing direct correlation to the flow velocity, in the form of direct reciprocity to the velocity and direct proportion to the length of the sensitive length of the detector. Autocorrelation of the function obtained by the overlap and pile-up of successive events is calculated and from the characteristic points in the autocorrelation function the axial velocity is inferred. The measurement is best when the probing beam is perpendicular to the flow.

18 Claims, 12 Drawing Sheets

OTHER PUBLICATIONS

"Dual Frequency Ultrasonic Fluid Flowmeter," Noble, The Review Of Scientific Instruments, vol. 39, No. 9, Sep., 1968, pp. 1327–1331.

"A Phase–Shift Ultrasonic Flowmeter," Zarnstorff, IRE Transactions On Biomedical Electronics, Jul. 1962, pp. 199–203.

"A New Ultrasonic Flowmeter For Intravascular Application," Plass, IEEE Transactions On Biomedical Engineering, BME–20, No. 1, 1973, pp. 154–156.

"Probability, Random Variables, and Stochastic Processes," Papoulis, pp. 358–359.

"Bioelectric Phenomena" Plonsey et al., Chapter on Electrochemistry and electrodes, pp. 23–77.

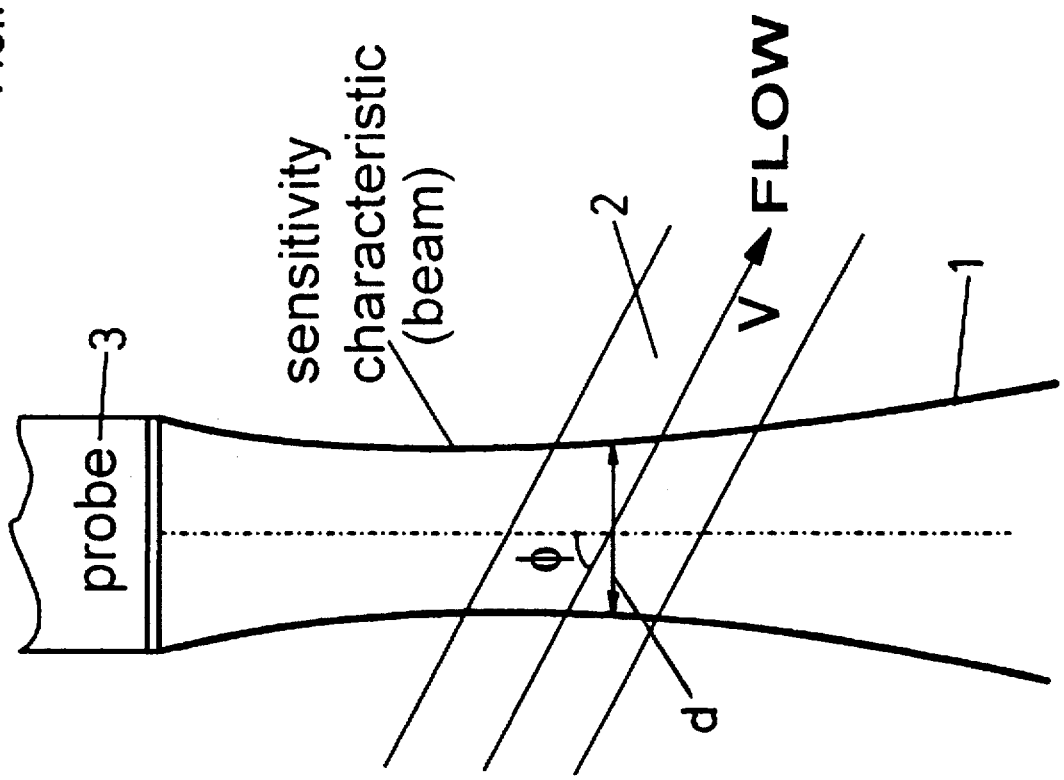
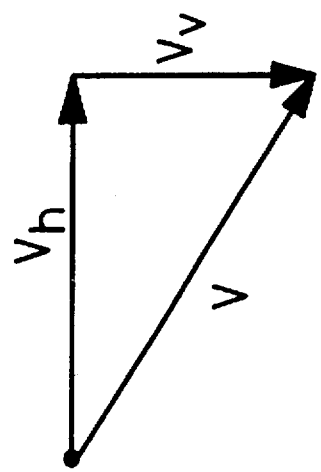
FIG.1

BLOOD FLOW MEASUREMENT DEVICE

FIELD OF INVENTION

The invention pertains to medical technology. It relates to fluid flow measurement in the field of medicine, and in particular to a blood flow measurement device.

BACKGROUND AND PRIOR ART

Fluid flow measurement plays an important part in modern medicine. This applies both to pure diagnostic procedures as well as to direct control of disease treatment. The various fluids which are, in this sense, of interest in the human body are very different in properties and include blood, pus, urine, inhaled and exhaled air, drug infusions, etc. In all the cases there exists a possibility of measurement of the flow using the Doppler effect provided there exist a wave reflecting or transmitting entity within the said liquid. A basic property of the Doppler effect is that it takes place if there exists a velocity along the line connecting the wave transmitter and its receiver. For plane waves, the Doppler effect equals zero if the probing waves are at 90° to the direction of movement of the said fluid. This means that only the velocity component projected to the line connecting the wave transmitter and its receiver is measured. This limitation applies strictly only to plane waves, while for bundled waves (beams) one can theoretically obtain a low frequency Doppler effect due to the fact that the wave fronts in a beam are not plane (Censor D., W. L. Newhouse, T. Wonz, H. V. Ortega: Theory of Ultrasound Doppler Spectra Velocimetry for Arbitrary Beam and Flow Configurations, IEEE Trans. on Biomedical Engineering, 35 (1988)740). This, however, is a part of frequency spectrum which is fully within the Doppler shift frequency spectrum of other movements in the body, such as the movement of the blood vessel walls, movement of the liver due to the heart beats, breathing movements, etc. This makes the cited phenomenon hard (and often impossible) to use, and in particular to use when the measurement process is unattended by interpreting humans (i.e. is used for some automatic regulation). Cross correlation techniques for velocity measurement exist in the form of wave transmitter-receiver array systems where the correlation among different lines-of-sight is used to obtain the velocity information. Due to the intrinsic physical impossibility to reduce the size of such a system the measurement is slowed down, thus correctly yielding only the low range of velocities encountered in the body. In addition, to the said velocity limitation the said cross correlation method is limited to pulsed wave mode in the case when velocities axial to the measurement device are measured. (Kasai, C., K. Namekawa: Real-time two-dimensional blood flow imaging using an autocorrelation technique, Proc. IEEE Ultrasonic Symposium 1985, IEEE, p. 953). While this approach yields Doppler equivalent results when used along the scanner line-of-sight and can even measure slow perpendicular velocities, it always requires full arrays of multiple transducers and is problematic in the measurement of the high velocities perpendicular to probing beams. In EP 228 070 assigned to Aloka Co.Ltd. the problem of the knowledge of the angle has been partially solved by using two probing beams under slightly different angles. The method requires fairly elaborate electronic systems and is usable only when the acoustic window is large enough to accommodate for the said two beams. In EP-144 968 and JP-228 330 the time domain calculation is adjusted for simplified calculation of the effects along the line-of-sight, yielding a Doppler-like result. The time domain calculation method has further been described in EP-92841, JP-070479 and U.S. Pat. No. 4,573,477 with the advantage of increasing and optimizing the sampling rate of the Doppler equivalent on-line measurement.

A larger number of prior inventors concern themselves with using the in-phase and quadrature detection components for further correlation calculations with improved results in Doppler-like procedures. This applies to EP-447597 which improves the measurable velocity by using multiple measurements and particular inter correlation calculations. In FR-2551213 the two quadrature demodulation components are used with two auxiliary oscillators to obtain a Doppler equivalent result. In EP-266998 and U.S. Pat. No. 4,790,323 the quadrature detection components are on-line compared and yield a better turbulence estimation in Doppler measurements.

Yet other methods which use correlation calculations have been used for different purposes and ways. For example in DE-3544477 and GB-2170972 the autocorrelation calculation between the two Doppler shift components are used to reduce noise. Quadrature detectors and mixing oscillators in conjunction with autocorrelation calculation are used in EP-140726 to optimize the number of samples and adjust them to flow velocity.

Calculations and measurements including transit time may be used to obtain the Doppler measured velocity profile as in EP-150672 where two beams at different angles are used to ascertain the position of the measurement volume and profile assessment. Other principles, such as a heating and cooling measurement system as in WO-9215239 are used for instantaneous velocity and viscosity measurement (this is, however, a fairly slow process).

Another possibility, to measure fluid velocity is the transit time method which does not rely on the scatter of ultrasound from red blood cells, but on the fact that ultrasound propagates through moving medium at a different speed compared to the speed in a still medium. Instruments based on this phenomenon have been described in a number of published works on flow measurement devices ( e.g. potentially implantable devices like one described by Franklin, D. L., Baker, D. W., Rushmer, R. F.: Pulsed ultrasonic transit time flowmeter, IRE Trans. Bio-Med. Electron. 9: p.44, 1962; dual frequency devices, e.g. Noble F. W.: Dual Frequency Ultrasonic Fluid Flowmeter, The Rev. of Scientific Instruments, 39, no. 9, (1968), p. 1327 and intravascular, implantable devices have been described using the same principle Plass, K. G.: A New Ultrasonic Flowmeter for Intravascular Applications, IEEE Trans. on Bio-Med. Eng., BME-20, no. 1, (1973), p.154, and finally, particular types of interferometry, the phase-shift of upstream and downstream propagating ultrasound has been described in Zarnstorff, W. C., Castillo, C. A., Crumpton, C. W.: A Phase-Shift Ultrasonic Flowmeter, IRE Trans. on Bio-Med. Electronics, 9, (1962), pp 199–203). This approach was abandoned when the sensitivity of ultrasound transducers and preamplifiers was improved enough in order to use the Doppler effect. The main reason was apparently that the said transit time devices always had to use two oppositely positioned transducers, making them less practical for implantation and usually useless for application from the body surface. Although this approach is now very rarely used, its potentials wait to be reevaluated with the improved materials technology. Some of such a development can be seen in U.S. Pat. No. 4,227,407 to Drost who uses the previously described transit-time phenomena for interferometric blood flow measurement, with the disadvantage of having to either exactly know the dimensions of the blood vessel or to have two implanted transducers.

U.S. Pat. No. 4,978,863 discloses an apparatus for determining flow rates of a fluid medium containing particles capable of backscattering light. The apparatus comprises a single probe means for illuminating a single, finite and symmetrical sensor field of said medium with light capable of being backscattered by said particles, said probe means including means for collecting backscattered light from said illuminated sensor field, means for converting said collected backscattered light into voltage waveforms and autocorrelation means for measuring the bandwidth of said waveforms at discrete points in time to determine fluid medium flow rates. Each discrete point in time establishes a time delay corresponding to 50% the decorrelation decay between initial and final values. Each time delay corresponding to 50% decorrelation is considered to be inversely proportional to the approximately average flow rate in the asymmetrically illuminated part of the stream.

EP-A-0 474 957 describes a blood flow measurement device according to the preamble of claim 1, wherein at least one Doppler measurement ultrasonic piezoelectric transducer means is arranged and mounted onto a catheter at the circumference thereof in a manner as to be able of generating an essential narrow directivity characteristic adjacent to the catheter. In one embodiment two transducer means are arranged, spaced apart from each other whereby the directivity characteristics cross each other to form a sensitivity volume.

It is an object of the present invention to provide an improved blood flow measurement device particularly suitable for cases when the angle between the flow and the wave beam or other sensing directivity functions used for the measurement approaches 90° or is exactly 90° and when the velocity direction is known or immaterial but the measurement of high velocities is important.

This object is attained by the blood flow measurement device according to claim 1. Preferred embodiments are described in the dependent claims.

SUMMARY OF THE INVENTION

A blood flow velocity measurement device is devised where there exist such entities within the fluid which are detectable when axially flowing (passing) by an appropriate detector of known and well defined dimensions. The said entities, when flowing by the said detector, induce a known single response, the response bearing direct correlation to the flow velocity, in the form of direct reciprocity to the said velocity and direct proportion to the length of the sensitive length of the said detector. Autocorrelation of the function obtained by the overlap and pile-up of successive events is calculated and from the characteristic points in the said autocorrelation function the axial velocity is inferred. The measurement is best when the probing beam is perpendicular to the flow.

An undirectional (single-side-band) device for measuring fluid flow velocity at 90° has been invented. The device applies to any fluid which contains elements (further called scatterers) which can be detected as distinctive entities by some method with well defined directivity characteristics. The device consists of a detector (or detector set) capable of detecting the said entities as they enter the sensitivity volume (within the sensitivity characteristic) as well as the moment when they leave the sensitivity volume (further called beam). The velocity of the fluid which passes through the sensitive volume (crossing it by its width) is the ratio of the sensitivity volume width and the time spent within it. For the normal case when the number of scatterers is so large that their crossing times overlap, the resulting signal is a combination of overlapped single crossing characteristics. The information about the crossing velocity is extracted by on-line calculation of the autocorrelation function of the described function of the overlapped crossing signals of a multitude of scatterers. The information of the single crossing time across the beam is, depending on the signal processing type, the delay time at the autocorrelation function zero crossing or its negative minimum (for positive crossing signals). The type of scatterers and the type of beam are basically irrelevant, but include pulsed wave and continuous wave ultrasound with ultrasound scatterers, light waves and light scatterers, detectors of ion clusters and ion clusters in liquid, magnetism detectors (inductive or otherwise) with ferromagnetic particles dispersed in the liquid, etc.

SHORT DESCRIPTION OF FIGURES

FIG. 1 represents a general situation where a sensing beam is transmitted into flowing fluid at a general angle and where the same transmitter is used for reception of the reflected waves.

DETAILED DESCRIPTION OF THE EMBODIMENTS

Referring to FIG. 1 we can describe the basic principle of the velocity measurement device as follows. The beam 1 shown here is in fact a sensing directivity characteristic of a general probing device 3 which may be attained with or without the use of any sort of waves. A detectable entity (e.g. a scatterer of ultrasound waves) passes the area occupied by the sensitivity characteristic 1, e.g. an ultrasound beam, at the point where the width of the beam equals d. The scatterer passes at a general angle $\phi$. The velocity V of the scatterer can be divided into components $V_h$ and $V_v$. The velocity component $V_h$ equals to the width d divided by the time the scatterer spends within the width d. The time spent within the beam can be measured by electronic circuits which detect the presence or the absence of the scatterer within the beam. The velocity component $V_v$ can not be measured in this way. Let it be noted that this measurement method yields a means of measuring the velocity component perpendicular to what is possible with the Doppler method, i.e. the Doppler effect for plane waves equals zero if the velocity is purely $V_h$. Unless the scatterer velocity is exactly along the beam axis, the total velocity can be calculated from the, thus measured, velocity $V_h$ by division with the sine of the angle $\phi$. It is important to note that in case of one single beam the direction of the, thus measured velocity $V_h$ can not be inferred from this measurement. On the other hand this method yields the absolute value of the said velocity component in the physically fastest possible way.

Now, if there are more than one scatterers passing through the beam, and if their appearance is dense enough, the signals which signal their presence within the beam may overlap. In fact, if there is a large multitude of such scatterers, the individual features of the signal as individual scatterers enter and leave the beam will apparently be lost within the pile-up variable signal.

However, the autocorrelation function of such a pile-up process must by mathematical laws contain a characteristic point, a discontinuity or extreme at the autocorrelation delay time equal to the time needed for individual scatterers to pass across the beam width d. The autocorrelation function is defined as the stochastic expectation of the values of a random process that are the delay time τ apart and, which are multiplied by each other. (A. Papoulis: Probability, Random Variables and Stochastic Processes: McGraw Hill Inc., 1965., page 359).

Figure 2:
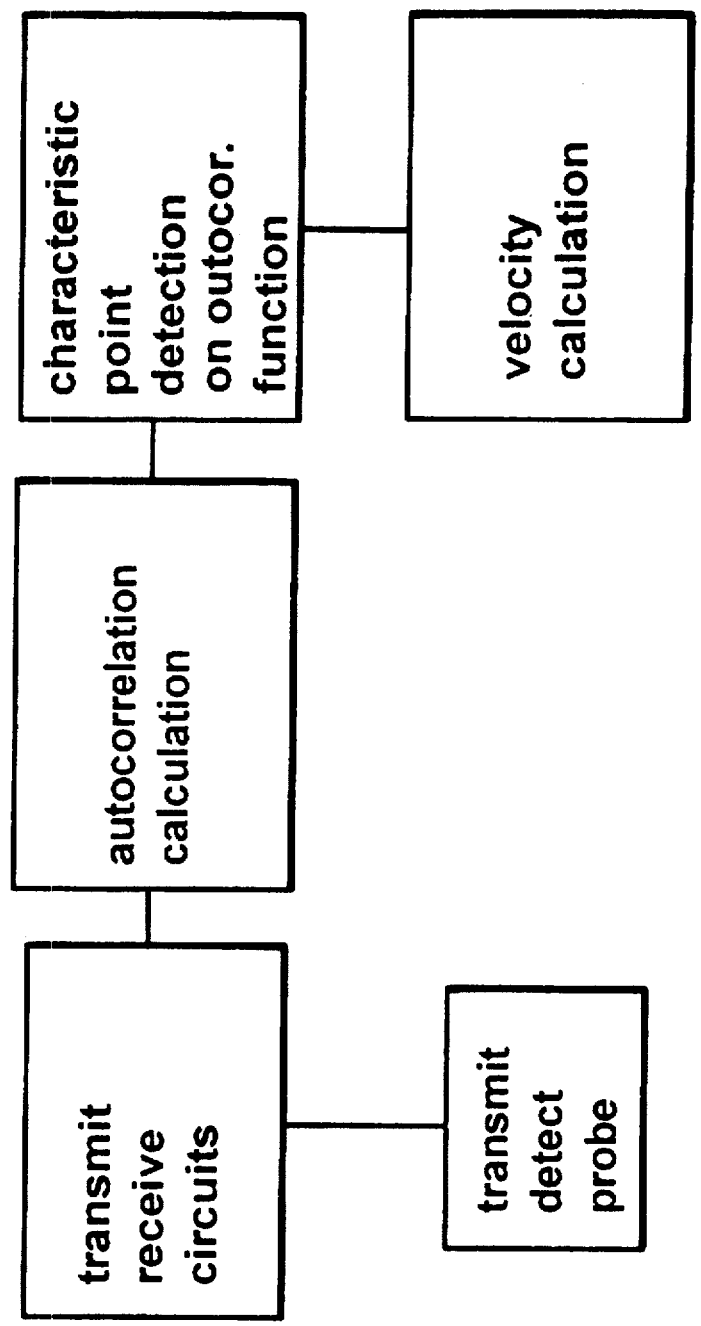
FIG. 2 represents a block diagram of a device capable of using the data from the waves incident from flowing fluid for flow measurement as per FIG. 1.

Therefore, referring to FIG. 2, the signals detected from the flow of a scattering medium are fed to an autocorrelation function calculator (digital or analogue). The time period until the occurrence of the characteristic point, normally the first minimum of the autocorrelation function is taken to be of the value equal to the time needed by the said scatterer to cross the distance d. Velocity is calculated by division of the width d of the said beam 1 with the thus measured time of occurrence of the characteristic point.

These and the following calculations and evaluations may be carried out in a suitable information processing device and be implemented by hard—and/or software, or by hardware alone.

Figure 3:
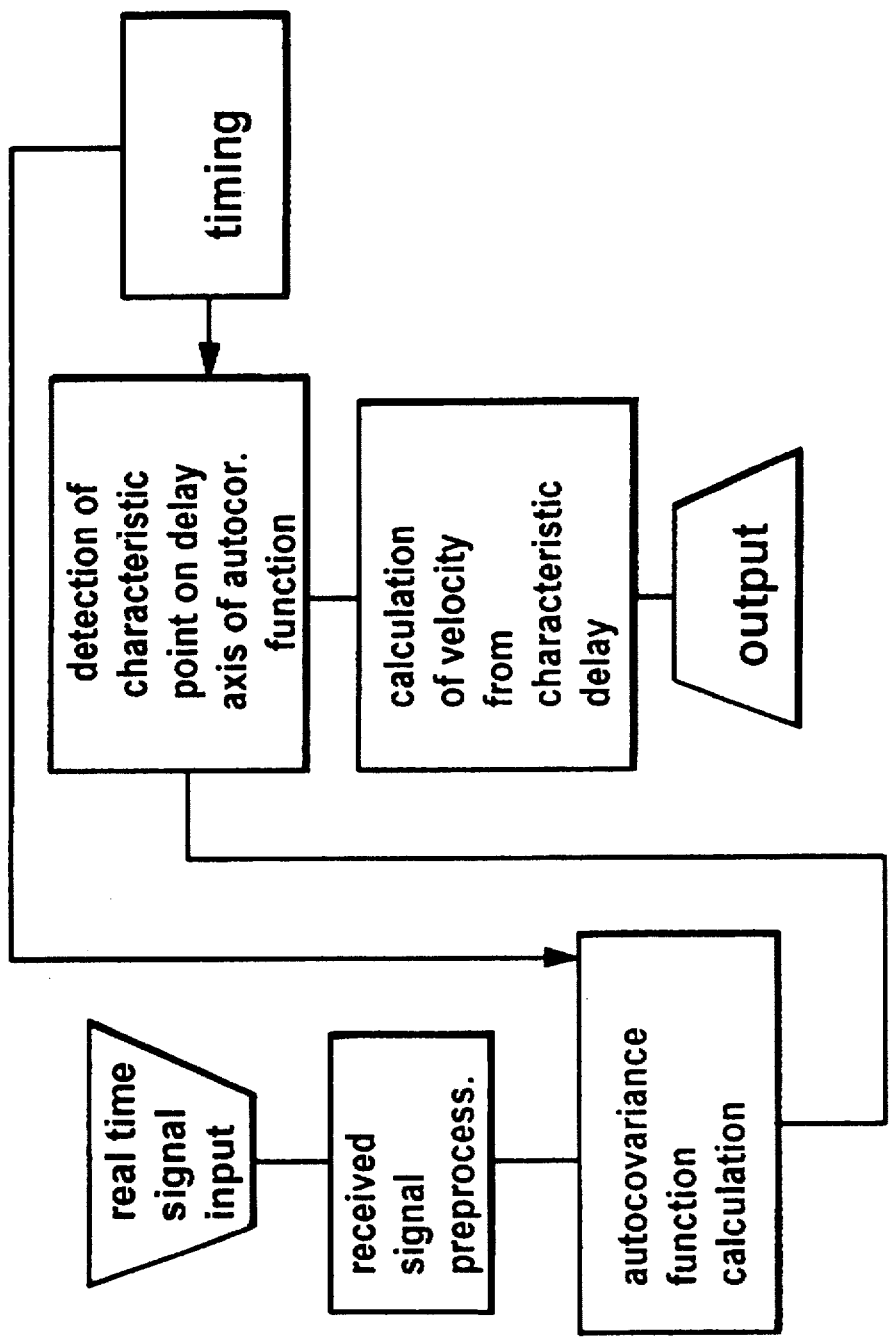
FIG. 3 represents the information flow diagram implemented when all or a part of the functions are performed with a computer (digital or analogue).

Referring to FIG. 3, a flow diagram for the calculation is devised as follows: The signal reflected from the flow area of interest in the flow 2 is input in real time. The signal is preprocessed, e.g. differentiated, frequency filtered, etc. Autocorrelation or autocovariance are calculated on the inflowing data. A timer circuit induces evaluation of thus gathered autocorrelation function and the search for the characteristic point, i.e. the first discontinuity which occurs at the point where the delay τ is equal to the transition time of a single scatterer across the beam 1 of FIG. 1. The beam width d is divided by the resultant time which yields the required velocity component $V_h$. For single scatterer signal starting with a positive rise and ending with a decrease to initial level, the said characteristic delay appears at the delay point where the negative slope of the autocorrelation function changes the slope from the initial negative slope to zero or positive slope. Thus the characteristic delay can be detected by detecting this change in the slope of the autocorrelation function.

Figure 4:
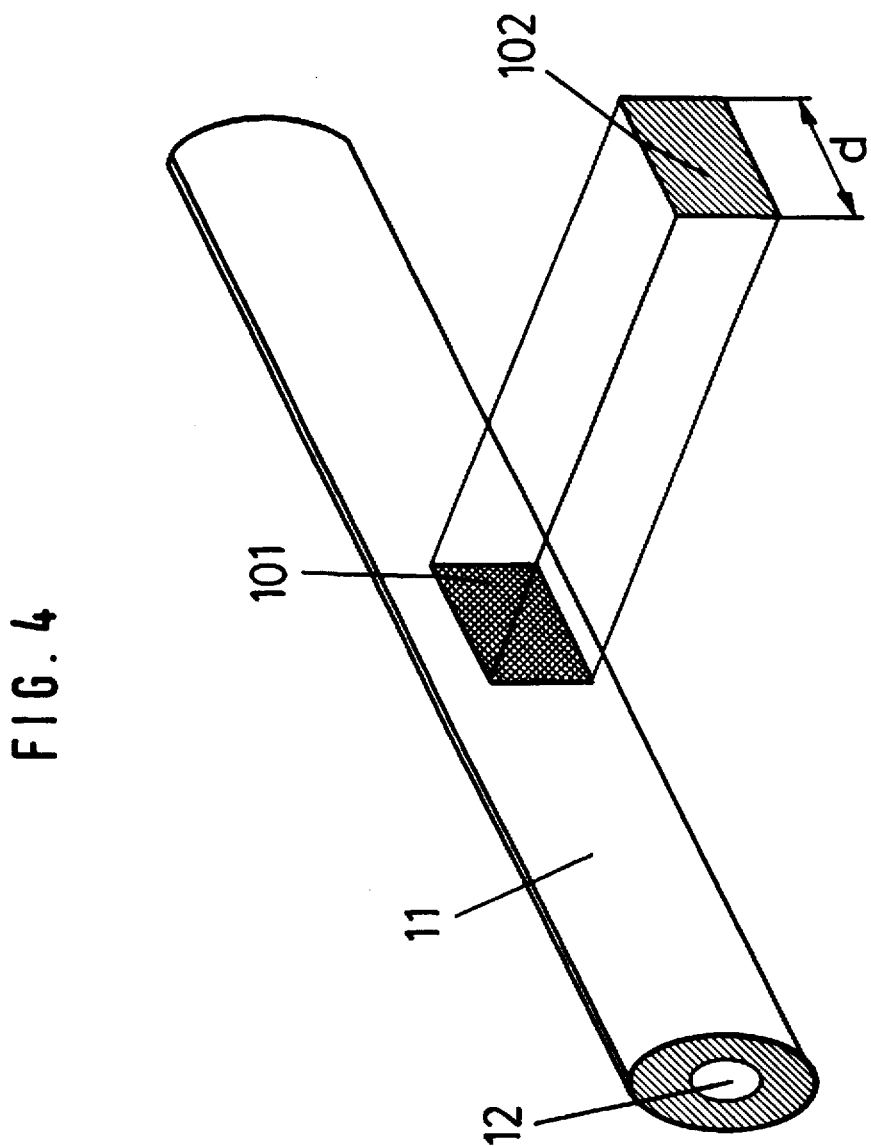
FIG. 4 represents a perspective illustration of an ultrasonic transmitter receiver transducer mounted onto an intraluminal catheter.

Referring to FIG. 4 showing the preferred embodiment of the invention (best mode), a device 101 generating a sensitivity area 102 is mounted onto a catheter means 11, the said sensitivity area having a characteristic axial (for the catheter) dimension d. The sensitivity characteristic is for simplicity shown as square, although it can have any physical form characteristic of wave beams created by directional antennas. The catheter means 11 can have a lumen 12 to accommodate for different functions including that of bringing to and taking away of signals for the device 101. The device 101 comprises an ultrasonic transmitter receiver transducer which can be used for echo detection of particles flowing parallel to the catheter axis and crossing the sensitivity area 102. The same said device serves both as the transmitter and as the receiver of the waves. Width d is the characteristic dimension which appears in the velocity calculations.

Figure 5:
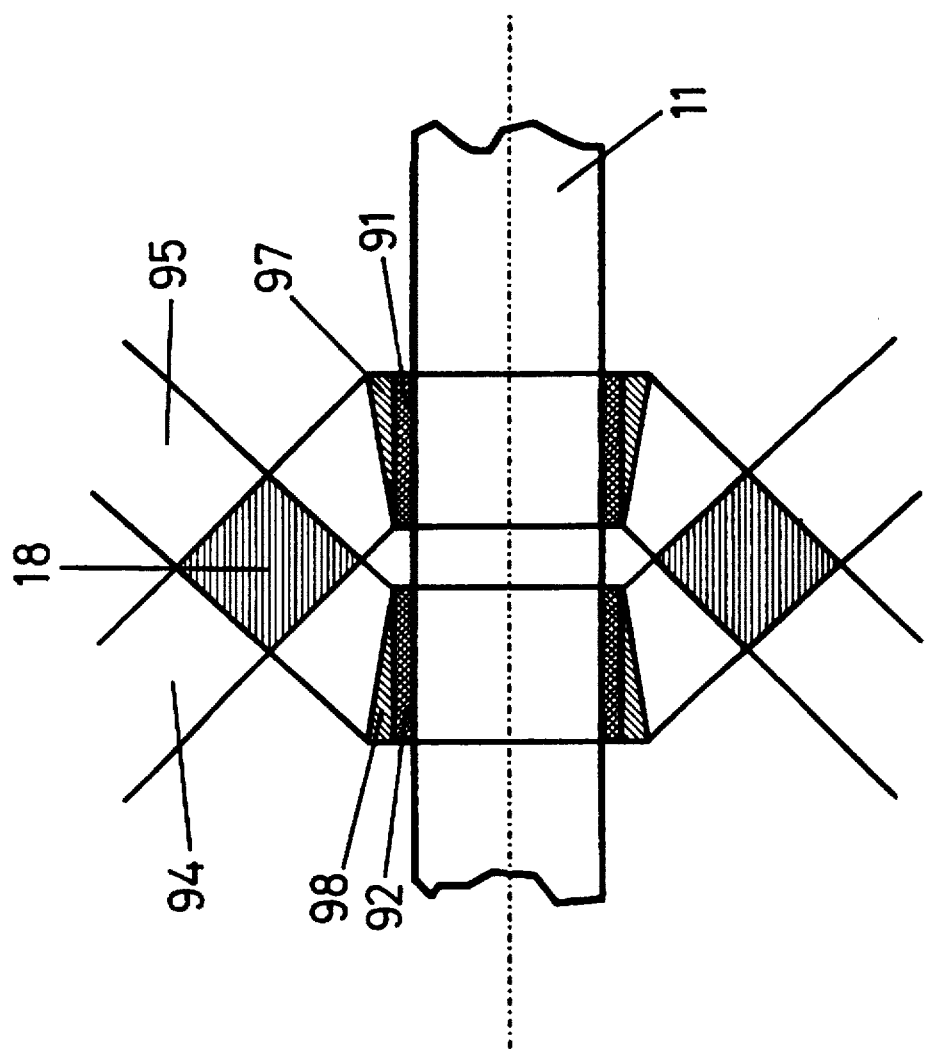
FIG. 5 represents an illustration of two piezoelectric transducers mounted onto a catheter.

FIG. 5 represents an illustration of two piezoelectric transducers mounted with one of their dimensions, preferably with their longest dimensions parallel onto a catheter where one of them is used as continuous wave transmitter and the other as a continuous wave receiver of waves scattered from the axially flowing fluid from within the sensitive area 18 which is the cross section of the transmission characteristic 94 and reception characteristic 95 obtained by tilting the beams from the said transducers by the use of tilting devices (lenses) 97 and 98.

Referring to FIG. 5, we can define a sensitive area in the sense of the previous text by application of two cylindric or otherwise formed piezoelectric transducers 91 and 92 which have glued on or otherwise fixed ultrasound beam tilting lenses 98 and 97 respectively which tilt the directivity characteristics 94 and 95 respectively, of the two devices in such a way as to overlap within an area 18. This area 18 has the properties of the generally outlined area 102 from FIG. 4 or the generalized beam of FIG. 1. The sensitivity area can be obtained by continuous transmission of waves from one of the said transducers (e.g. 91) and reception of the scattered waves by the other of the transducers (e.g. 92). The transmission and reception can be continuous or synchronized pulsed transmission and reception. The electrical signals needed to actuate the said transducers are fed to them and taken from them to appropriate electronic circuits by conductors built into the catheter means 11 body (not shown).

Figure 6:
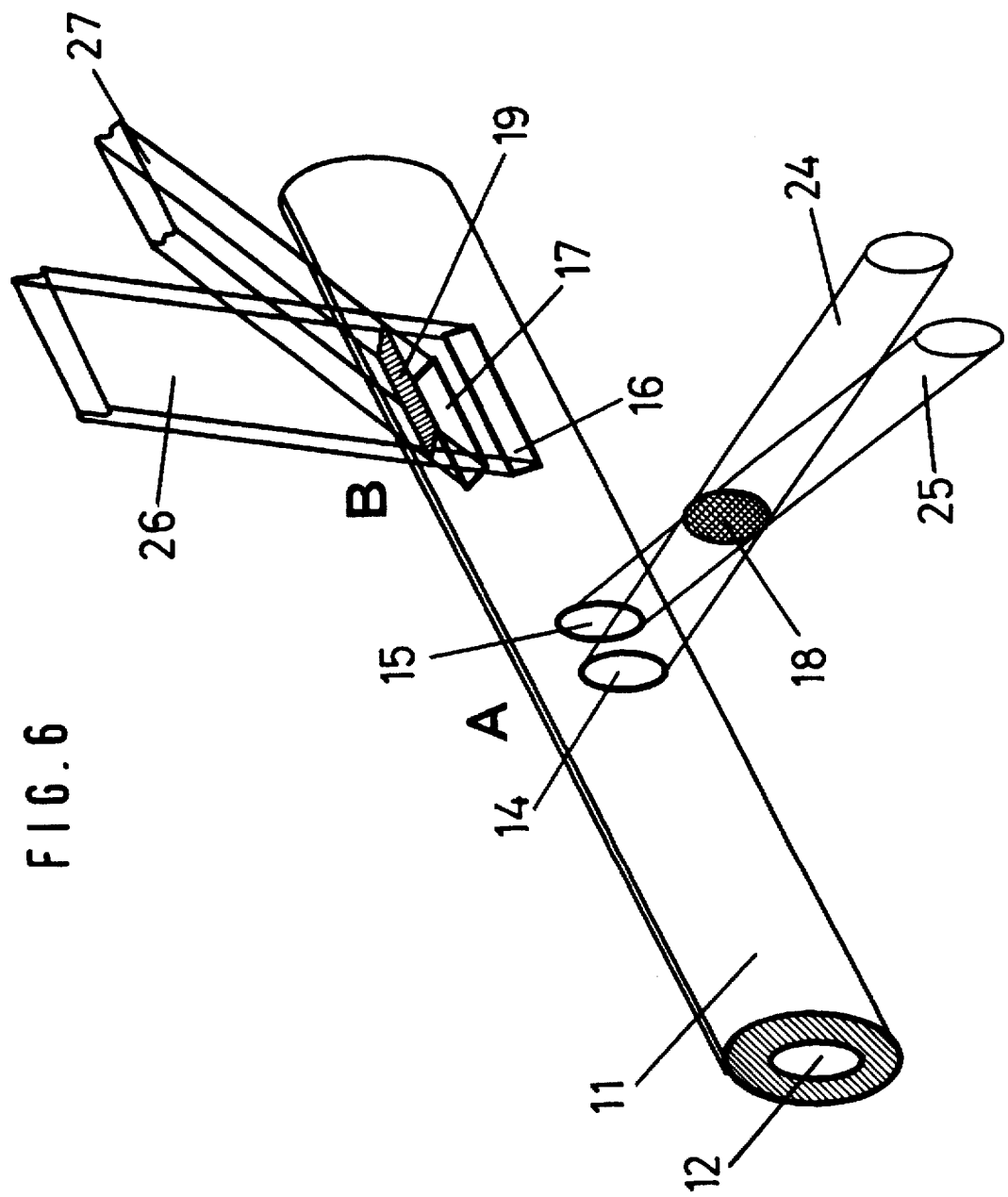
FIG. 6 represents an illustration of paired wave (piezoelectric or light) transducers mounted onto a catheter.

FIG. 6 represents an illustration of paired wave (piezoelectric or light) transducers (14 and 15 in case A and of a different form 16 and 17 in case B) mounted onto a catheter, arranged differently from those from FIG. 5, where one of them is used as continuous wave transmitter and the other as a continuous wave receiver of waves scattered from the axially flowing fluid. The directivity characteristics in case A are designated by 25 and 24 and in case B by 26 and 27, while their intersections are designated by (18) and (19) respectively. The two sets (embodiments) of transmitters and receivers of waves (light or ultrasound) are positioned in such a way as to enable one of the devices to transmit the said waves into the scattering medium and the other device to receive the scattered waves from the area where the two directivity functions overlap.

Referring to FIG. 6 more in detail, we see an illustration of a catheter means 11 with a lumen 12 with two embodiments of light transmitter-receiver sets, A and B. In embodiment A the transmitter and the receiver of light waves 14 and 15 respectively are preferably focussed and their directivity characteristics 24 and 25 respectively overlap at an area 18. In the embodiment B the wave transmitter 16 and the receiver 17 have been shown of a square form with directivity characteristics 26 and 27 overlapping within an area 19 of an essentially square form. The essentially square form of the sensitivity area has the property of having equal transit lengths for all the scatterers flowing within the fluid around the said catheter means in axial direction relative to the said catheter means. The light transmitter and receiver have the property of being able to transmit and receive the light waves.

Figure 7:
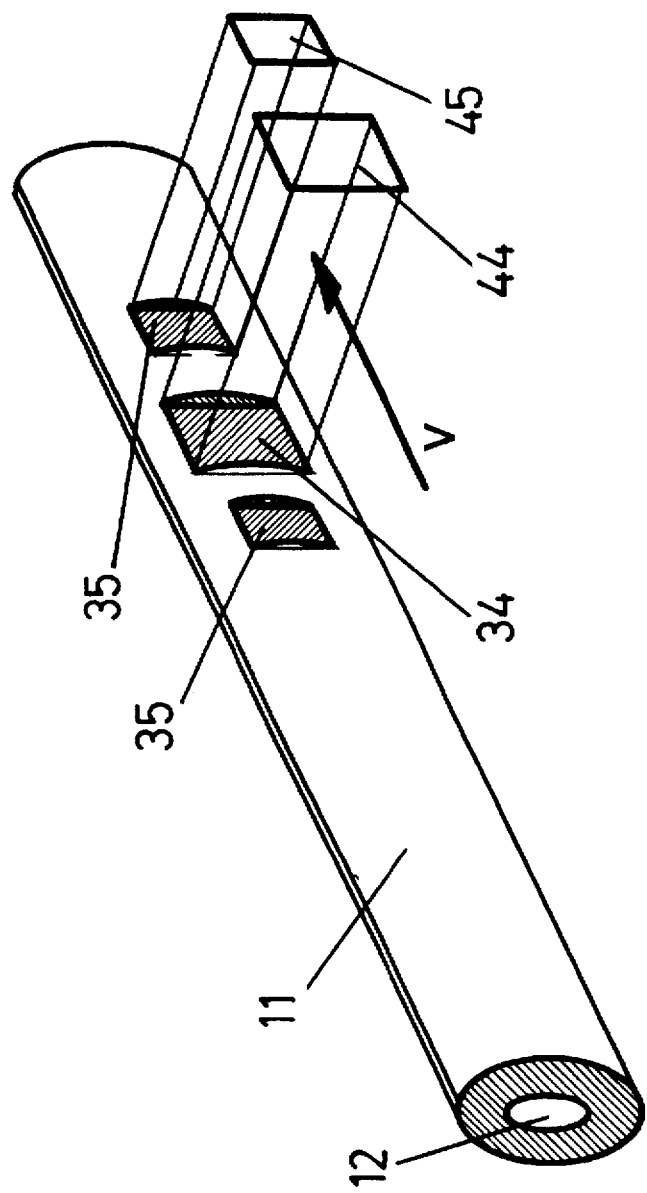
FIG. 7 represents a perspective illustration of a general generating device means mounted on a catheter means capable of generation and/or injection into flowing fluid of entities.

Referring to FIG. 7, there is an illustration of the said catheter 11 having mounted thereon a general property generator 34 capable of generation and/or injection into flowing fluid of entities (e.g. ions or magnetic dipoles) detectable within sensitivity characteristics 45 of reception devices means 35 and connected to outside circuits via leads put into the lumen 12 of the catheter means. This ig. represents an illustration of an apparatus in which one device generates a detectable property in the liquid, (e.g. ionizes it), and the other detector means measures the amount of the axially passing detectable entities (e.g. ion clusters) using the method of extracting the velocity data outlined in FIG. 1. The generator and the two general property detectors 35 have respective directivity functions 44 and 45. The property (e.g. ionization, magnetization or the like) is imposed onto the particles flowing in the liquid at velocity V and detected within the sensitivity area 45 of the property detectors. The device principle outlined in the description of FIG. 1 to 3 is then applied to the signal thus obtained.

Figure 8:
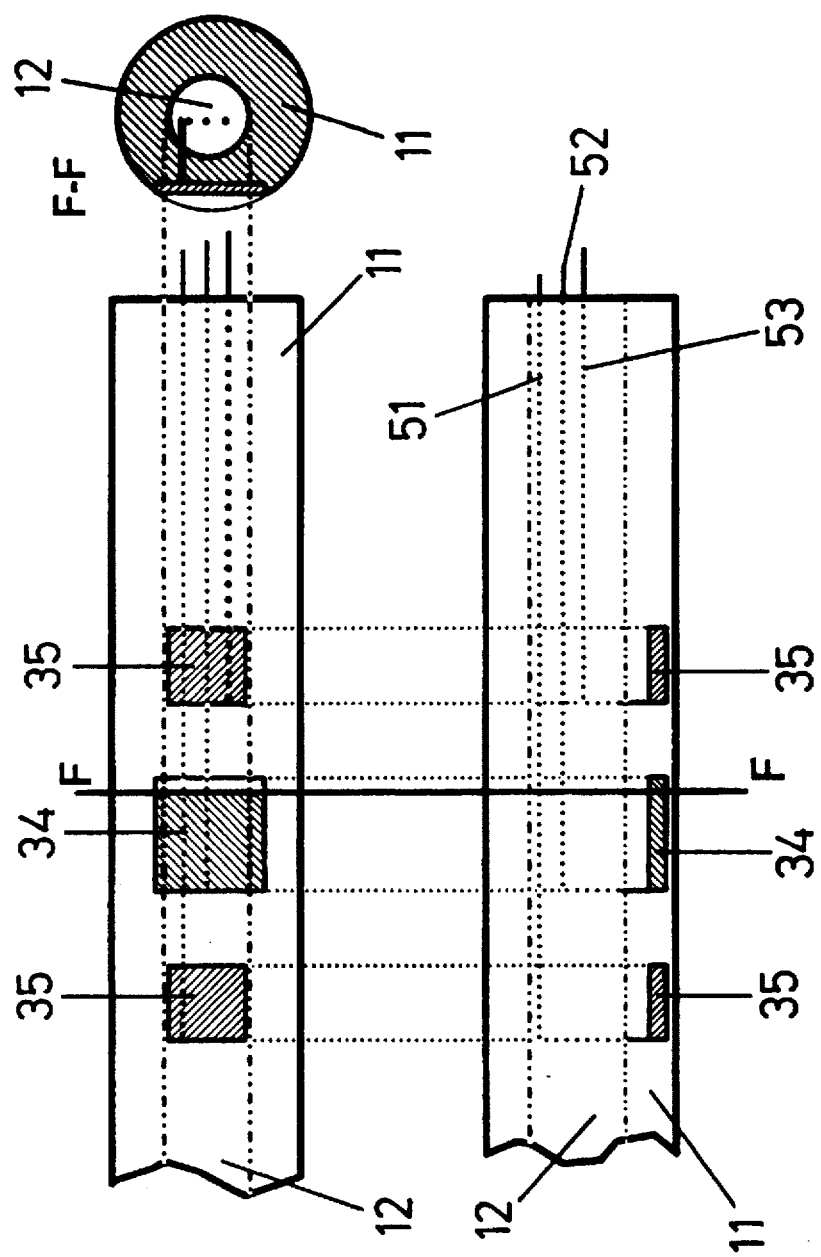
FIG. 8 represents a three projection illustration of the device illustrated in FIG. 7 with connection leads means.

Referring to FIG. 8, which is a three projection illustration of the device from FIG. 7, illustrating that the said generation means 34 and the said reception means 35, respectively shall be connected to the proximal side of the said catheter 11 using general conductors 51, 52, 53 led through the lumen 12 and connected or connectable to electronic circuits performing the operations outlined in FIG. 2 and 3.

Figure 9:
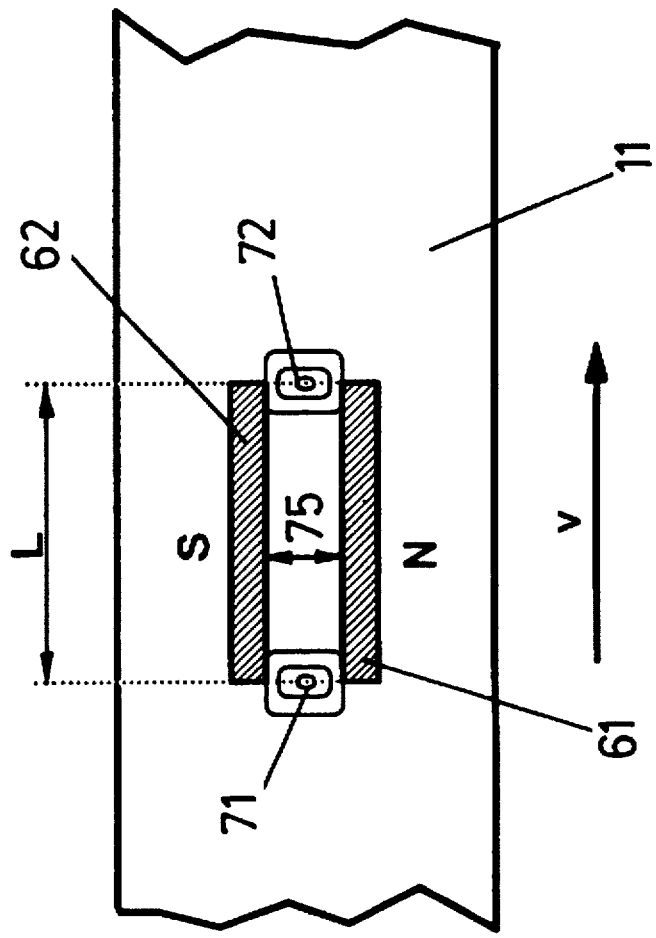
FIG. 9 is an illustration of one embodiment of a device capable of detecting entities with magnetic polarization properties.

FIG. 9 is an illustration of one embodiment of a device capable of detecting entities with magnetic polarization properties flowing axially with regard to the catheter means 11 by virtue of orienting the said magnetic dipoles between the south S and north N pole of a magnet with a gap 75 between them and of a length L and by detecting the change in magnetization of the dipoles by sensing coils 71 and 72.

In this embodiment of a magnetic detector of magnetizable entities flowing axially with the liquid parallel to dimension L in FIG. 9 such magnetizable entities (e.g. particles) abruptly change their magnetic orientation when entering the magnetic field between the south S and north N pole of a magnet where the distance among the said pole pieces is known and defined 75. The sudden change of the magnetic polarization and depolarization at the entrance and at the exit can be detected by said detection coils 71 and 72 and fed to signal processing systems according to FIG. 2 and 3 in order to calculate the axial velocity of the said flowing particles.

Figure 10:
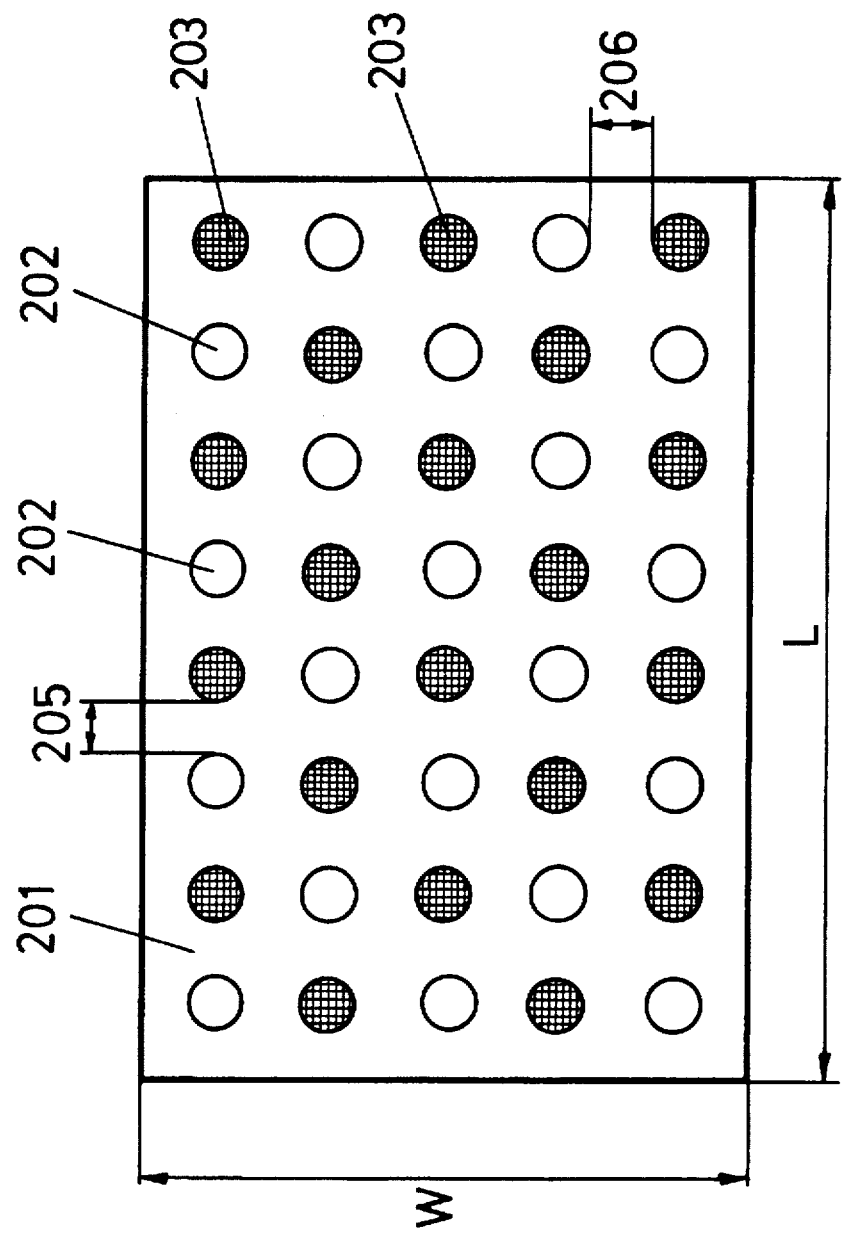
FIG. 10 represents an illustration of a light transmitting-receiving matrix device.

FIG. 10 represents an illustration of a light transmitting-receiving matrix device where on a support plate 201 light transmitters 202 and light receivers 203 are arranged in a dense way such as to yield a homogeneous light field in front of the device and the scattering of the light waves by scatterers flowing in front of the device are detected continuously by receivers 202 which jointly act as one receiver of the length L and width W. Distances 205 and 206 can be made as small as necessary.

Referring to FIG. 10 more in detail, the composite light transmitter-receiver device as seen from the front, comprises light transmitting devices 202, e.g. LEDs and light reception devices 203, e.g. photo transistors packed densely enough (with distances 205 and 206 small enough) to act as a joint transmitter-receiver device detecting light scatterers as they pass in front of the device. The devices 202 and 203 are preferably defocussed in such a way as to create a quasi continuous field of light in front of the whole device. If the flow is parallel to the dimension L then this is the characteristic dimension in the sense of calculation outlined in FIG. 2 and 3, and the same relates to dimension W if the flow is parallel to it.

Figure 11:
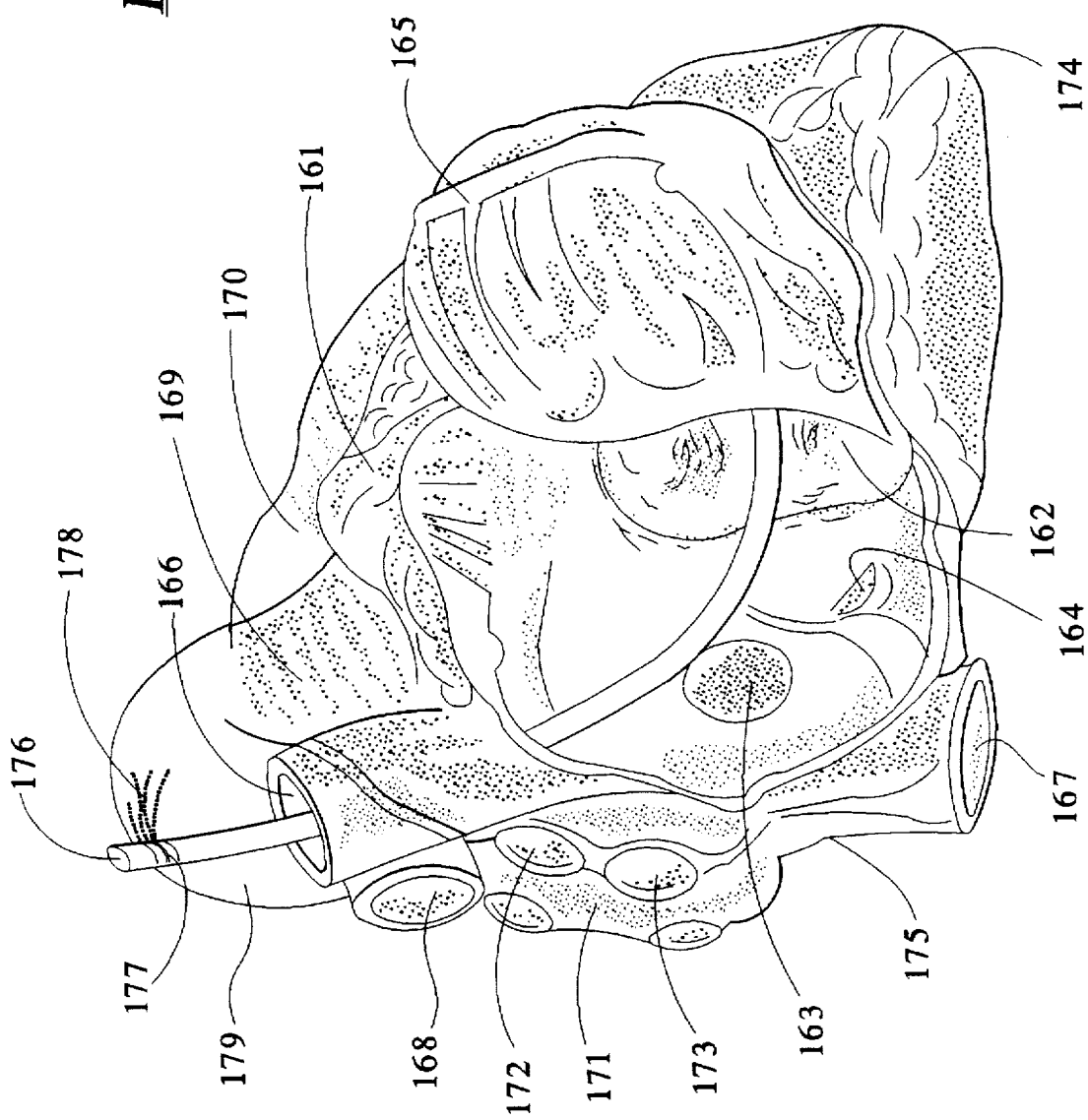
FIG. 11 shows the heart having implanted a lead comprising the aortic flow measurement assembly.
Figure 12:
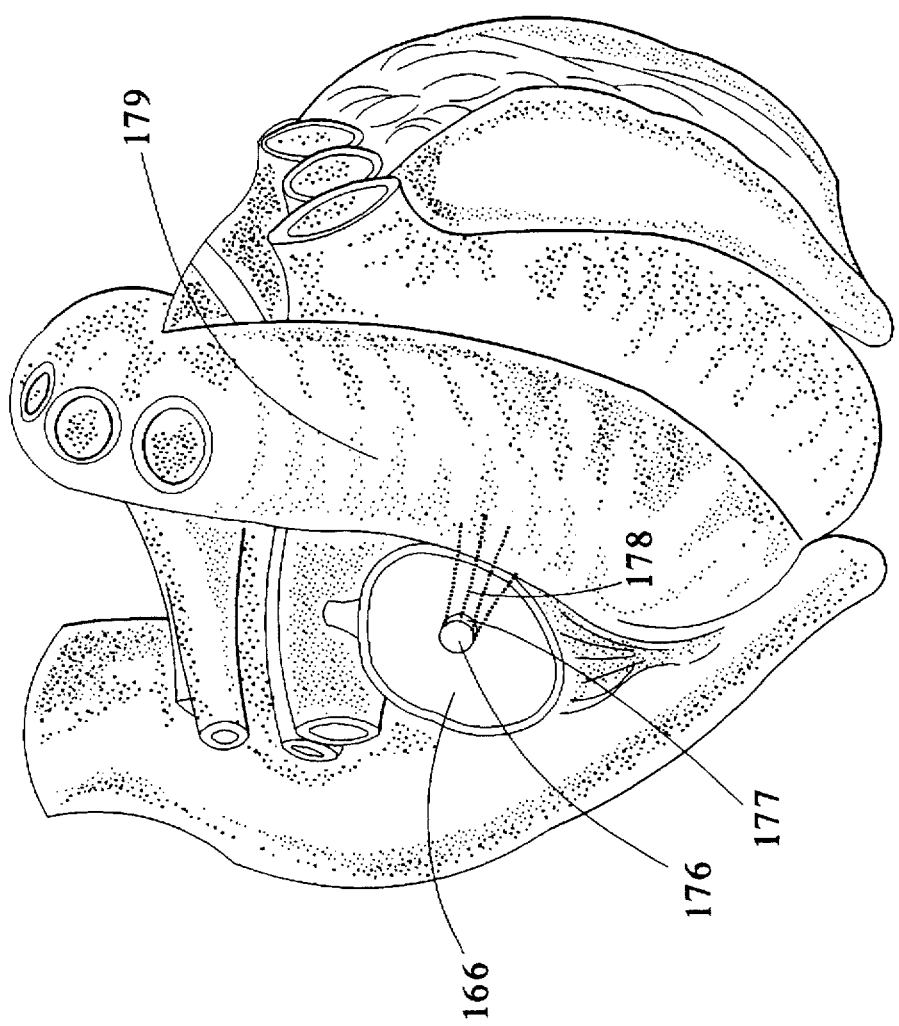
FIG. 12 shows the caudal view on the heart illustrating the aortic flow measurement.

FIG. 11 and 12 disclose the principle of aortic flow measurement by means of the transducer assembly disclosed in previous Fig. and relevant description. The aortic flow measurement can be utilized for cardiac electrotherapy control. Disclosed measurement system is feasible to be incorporated within an implantable electrotherapy device.

As it is known in the art, every ventricular contraction produces the aortic flow wave. Accordingly, the stroke volume can be calculated from the waveform of the aortic flow, assuming that the aortic cross-section area is a known previously measured parameter. Therefore this device can be used for rate variation in rate responsive pacing, pacing capture monitoring, tachycardia detection as well as differentiation, ventricular fibrillation detection, and left ventricular systolic myocardial function estimation. These physiological principles were disclosed in numerous prior art of cardiology and echocrdiography.

FIG. 11 shows the heart opened at the right atrial appendage 161. There are tricuspid valve 162, fossa ovalis 163, coronary sinus valve 164 and crista terminalis 165 within the right atrium. The vena cava superior 166 and the vena cava inferior 167 as well as the pulmonary artery 168 and the aorta 169 with truncus pulmonalis 170 are disclosed. The left atrium 171 with right superior pulmonary vein 172 as well as with right inferior pulmonary vein 173 are shown. The right ventricular apex 174 is disclosed as well as the residue of the pericardium 175. The pacemaker lead 176 is implanted through the vena cava superior 166 and right atrial cavity through the tricuspid valve 162 in the right ventricle with its tip (not shown) in the area of apex 174. The lead 176 comprises an ultrasonic transducer assembly 177 which produces the measurement ultrasonic field 178 directed towards the aortic arch 179.

FIG. 12 shows the caudal view on the heart having the analogous designations for same elements which are shown on previous FIG. 11. The lead 176 is implanted through the superior vena cava 166 as disclosed on this axial view. As it is clearly demonstrated in this projection, the ultrasonic measurement field 178 produced by transducer assembly 177 is directed towards the aortic arch 179. Ideal situation is disclosed, whereby ultrasonic beam is perpendicular towards the aortic flow.

We claim as our invention:

1. A blood flow measurement device for measuring a flow perpendicular to a probe beam, comprising:

a catheter insertable into a blood vessel in the body of a subject, said catheter having a distal end and a proximal end and a length extending therebetween;

at least one detecting device means mounted onto said catheter at a position along said length without impeding insertion of the catheter into the blood vessel, for emitting a probe beam having a directivity characteristic which defines a sensitivity volume for detecting entities flowing through said sensitivity volume and for generating detection signals corresponding to detection of said entities;

electronic circuitry means for measuring and performing calculations on the signals generated by said detecting device means to obtain calculation data signals; and evaluation means responsive to said calculation data signals for determining a velocity of flow of said entities therefrom, said electronic circuitry means comprising means for performing time autocorrelation calculations and said evaluation means comprising means for detecting a signal characteristic in said calculation data signals for obtaining a characteristic delay time within an autocorrelation function and for dividing the sensitivity volume in a direction of said flow with said characteristic delay time for identifying a velocity component of the blood flow in said direction.

2. A blood flow measurement device as claimed in claim 1 wherein said detecting device means comprises an ultrasonic transducer and means for operating said ultrasonic transducer in at least one of a pulse-echo mode and a continuous wave mode.

3. A blood flow measurement device as claimed in claim 2 wherein said ultrasonic transducer includes a plurality of piezoelectric transducer elements of different geometrical forms which, in combination, produce a defined directivity characteristic, said piezoelectric transducer elements being mounted onto said catheter.

4. A blood flow measurement device as claimed in claim 3 wherein said catheter has a longitudinal axis along said length thereof and wherein said piezoelectric transducer elements produce a directivity characteristic having an axis disposed substantially perpendicular to said longitudinal axis.

5. A blood flow measurement device as claimed in claim 4 wherein said means for operating said ultrasound transducer comprise means for operating said ultrasound transducer in said pulse-echo mode with a sensitivity for detecting ultrasound scattered from erythrocytes as said entities in said flow.

6. A blood flow measurement device as claimed in claim 3 wherein said plurality of piezoelectric transducer elements includes at least one pair of piezoelectric transducer elements, each piezoelectric transducer element in said at least one pair having a directivity characteristic and the respective directivity characteristics of said piezoelectric transducer elements in said at least one pair overlapping and defining a volume outside of said catheter comprising said sensitivity volume, and said piezoelectric transducer elements in said at least one pair each having a longest dimension which extends parallel to said length of said catheter.

7. A blood flow measurement device as claimed in claim 1 wherein said detecting device means comprise at least one pair of optical transducer elements, each optical transducer element in said pair having respective transmission and reception directivity characteristics, and the respective transmission and reception directivity characteristics of said optical transducers in said at least one pair overlapping and defining a volume outside of said catheter comprising said sensitivity volume.

8. A blood flow measurement device as claimed in claim 1 wherein said detecting device means comprise ion generator means for generating ions in blood in said blood vessel, and ion detector means, having said sensitivity volume disposed in front thereof, for detecting a density of ions in said sensitivity volume.

9. A blood flow measurement device as claimed in claim 1 wherein said detector device means comprise magnetic polarization detector means, having said sensitivity volume in front thereof, for detecting magnetically polarized entities in said sensitivity volume.

10. A blood flow measurement device as claimed in claim 9 wherein said magnetic polarization detector means comprise a ferromagnetic particle detection device having a length defining said sensitivity volume, said ferromagnetic particle detection device detecting a presence or absence of at least one ferromagnetic particle in said sensitivity volume.

11. A blood flow measurement device as claimed in claim 10 wherein said ferromagnetic particle detection device comprises a north-south polarized pole piece pair which generate a magnetic field in said sensitivity volume, and a pair of detection windings which detect changes in said magnetic field as a result of said at least one ferromagnetic particle entering and leaving said sensitivity volume.

12. A blood flow measurement device as claimed in claim 11 wherein said detecting device means comprise a light transmission-detection device disposed on a surface of said catheter and containing a plurality of densely packed light sources and detectors, each light source and detector having a directivity characteristic and the respective directivity characteristics of said light sources and detectors overlapping at a defined distance above said surface, and each light source and detector having a substantially inverse square sensitivity characteristic with respect to distance.

13. A blood flow measurement device as claimed in claim 11 wherein said catheter comprises electrical conductors running along said catheter from said detecting device means to the proximal end of said catheter.

14. A blood flow measurement device as claimed in claim 13 wherein said catheter comprises electrical connectors respectively terminating said conductors at said proximal end of said catheter.

15. A blood flow measurement device as claimed in claim 14 wherein said electronic circuitry means is disposed at said proximal end of said catheter, connected to said electrical connectors, and wherein said electronic circuitry means includes means for activating said at least one detecting device means and for detecting electrical signals from the activated detector device means.

16. A blood flow measurement device as claimed in claim 15 wherein said evaluation means are disposed at said proximal end of said catheter, connected to said electronic circuitry means.

17. A blood flow measurement device as claimed in claim 1 further comprising display means connected to said evaluation means for displaying a representation of said velocity component.

18. A blood flow measurement device as claimed in claim 1 further comprising transmission means, connected to said evaluation means, for transmitting a representation of said velocity component to a location remote from said evaluation means.

* * * * *